(12) United States Patent
Kim et al.

(10) Patent No.: US 9,787,113 B2
(45) Date of Patent: Oct. 10, 2017

(54) CHARGING APPARATUS FOR MOBILE DEVICE AND MULTI-STATION CHARGING APPARATUS USING THE SAME

(71) Applicant: Seoul Viosys Co., Ltd., Ansan-si (KR)

(72) Inventors: Jong-Rack Kim, Seoul (KR); Seong-Min Lee, Seoul (KR)

(73) Assignee: Seoul Viosys Co., Ltd., Ansan-si (KR)

( * ) Notice: Subject to any disclaimer, the term of this patent is extended or adjusted under 35 U.S.C. 154(b) by 300 days.

(21) Appl. No.: 14/541,538

(22) Filed: Nov. 14, 2014

(65) Prior Publication Data

US 2015/0137762 A1    May 21, 2015

(30) Foreign Application Priority Data

Nov. 15, 2013  (KR) .................. 10-2013-0138717
Sep. 5, 2014   (KR) .................. 10-2014-0118850

(51) Int. Cl.
| | | |
|---|---|---|
| *H02J 7/00* | (2006.01) | |
| *F21V 7/00* | (2006.01) | |
| *F21V 8/00* | (2006.01) | |
| *A61L 2/10* | (2006.01) | |
| *F21Y 115/10* | (2016.01) | |

(52) U.S. Cl.
CPC .............. *H02J 7/0044* (2013.01); *A61L 2/10* (2013.01); *F21V 7/0066* (2013.01); *G02B 6/0075* (2013.01); *F21Y 2115/10* (2016.08)

(58) Field of Classification Search
CPC .................................. H02J 7/0044; A61L 2/10
USPC ........................... 320/107, 115; 250/455.11
See application file for complete search history.

(56) References Cited

U.S. PATENT DOCUMENTS

| | | | | |
|---|---|---|---|---|
| 2005/0255895 A1* | 11/2005 | Lee | ....................... | G06F 1/1632 455/573 |
| 2010/0044582 A1* | 2/2010 | Cooper | ..................... | A61L 2/10 250/455.11 |
| 2013/0063922 A1* | 3/2013 | La Porte | ................... | A61L 2/10 361/807 |

FOREIGN PATENT DOCUMENTS

| | | |
|---|---|---|
| CN | 101202457 A | 6/2008 |
| CN | 201638104 U | 11/2010 |
| CN | 202142883 U | 2/2012 |
| CN | 202353246 U | 7/2012 |
| CN | 202605362 U | 12/2012 |
| CN | 203707444 U | 7/2014 |
| KR | 20110083073 A | 7/2011 |
| WO | 2006022466 A1 | 3/2006 |

OTHER PUBLICATIONS

The State Intellectual Property Office of P.R. China, Chinese Patent Application No. 201410652673.5, The First Office Action, English translation, Jun. 22, 2016, 12 pages.

\* cited by examiner

*Primary Examiner* — Edward Tso
*Assistant Examiner* — Aaron Piggush
(74) *Attorney, Agent, or Firm* — Perkins Coie LLP

(57) ABSTRACT

Charging apparatuses are provided for charging mobile devices while sterilizing the mobile devices via UV illumination. Such a charging device can include a charging apparatus case having a slot structured to receive a mobile device. The front and rear surfaces of the mobile device are exposed to inner walls of the slot; and at least one UV light source can irradiate UV light onto the front and rear surfaces of the mobile device, which are exposed to the inner walls of the slot.

25 Claims, 9 Drawing Sheets

Charging Apparatus for Mobile Device and Multi-Station Charging Apparatus Using the Same

CROSS REFERENCE TO RELATED APPLICATION

This patent document claims the priorities and benefits of Korean Patent Application No. 10-2013-0138717, filed on Nov. 15, 2013, and Korean Patent Application No. 10-2014-0118850, filed on Sep. 5, 2014, the contents of which are incorporated by reference in their entirety as part of this patent document.

BACKGROUND

The technology disclosed in this patent document relates to a charging apparatus for charging a mobile device.

Recently, as various mobile devices are rapidly spreading, development for charging apparatuses capable of charging mobile devices has been actively conducted. The charging apparatuses for a mobile device may be classified into a wired charging type and a wireless charging type. In either type, a mobile device is charged in a state where the mobile device is supported by a support structure.

SUMMARY

Examples of implementations of the disclosed technology include a charging apparatus for a mobile device that includes a sterilization function, and a multi-station charging apparatus for charging mobile devices. The disclosed examples of charging apparatuses are capable of simultaneously or substantially simultaneously sterilizing both front and back surfaces of a mobile device in a state where the mobile device is mounted or docked on the charging apparatus. In addition, a multi-station charging apparatus with the sterilization function can include additional components, such as speakers, to provide multiple features in addition to charging and sterilization.

In one aspect, a charging apparatus for charging a mobile device based on the disclosed technology can include: a charging apparatus case including a slot structured to receive a mobile device into the slot with the front and rear surfaces of the mobile device exposed to inner walls of the slot; and at least one UV light source disposed on at least one of the inner walls of the slot and configured to irradiate UV light onto the front and rear surfaces of the mobile device, which are exposed to the inner walls of the slot. At least the front and rear surfaces are exposed in the slot so as to allow at least one UV light source to irradiate UV light onto the front and rear surfaces for sterilizing the irradiated surfaces.

In some implementations, the charging apparatus may include a charging port arranged at the bottom of the charging apparatus case. The charging port may include any one of a wired charging port and a wireless charging port.

In some implementations, the charging apparatus case may have a slide dock installed on the charging apparatus case with the slide dock structured to move between an inner predetermined position of the charging apparatus case and a position outside the charging apparatus case, and the charging port may be installed on the slide dock. A charging terminal installed on the slide dock is exposed to the outside in a state where the slide dock is drawn or moved to the outside from the inside of the charging apparatus case. The charging apparatus may further include a stopper interworking with the movement of the movable slide dock. When the slide dock is drawn or moved to the outside from inside the charging apparatus case, the stopper may be positioned in a slot having no corresponding charging terminal to prevent a mobile device from being inserted into the slot having no corresponding charging terminal.

In some implementations, the slot may have a guide installed so as to guide an object positioned in the slot to the charging port, and the guide may be formed of a material transmitting UV light.

In some implementations, the charging port may be installed on a rotating drum which rotates about an axis. When the rotating drum is rotated, the mobile device connected to the charging port may be rotated together to be obliquely placed in the slot to be slightly slanted. The rotating drum may be installed on the slide dock. The rotating drum may be rotated between at least first and second positions, and have an elastic body installed with the elastic body elastically supporting the rotating drum in a direction where the rotating drum is rotated from the second position to the first position. The rotating drum may be rotated between at least first and second positions, and include a power supply trigger device which is triggered to supply power to the UV light source when the rotating drum is located at the second position.

In some implementations, one of the charging apparatus case and the slide dock, which are movable relatively to each other, may include a power supply rail installed, and the other one not including the power supply rail may include power connection units connected to the at least one UV light source arranged in the slot. Based on the relative position between the charging apparatus case and the slide dock, the power connection units may be contacted with or isolated from the power supply rail. The at least one UV light source may include a UV LED. The charging apparatus may further include a secondary optical device provided at the front of the at least one UV light source and configured to control the diffusion angle and beam angle of the UV light source.

In some implementations, the UV light source may emit UV light at a wavelength of 100 nm to 400 nm.

In some implementations, the UV light source may include: a first UV light source arranged on an inner wall facing the front surface of the mobile device, and configured to irradiate UV light onto the front surface of the mobile device; and a second UV light source arranged on an inner wall facing the rear surface of the mobile device, and configured to irradiate UV light onto the rear surface of the mobile device. The first UV light source may be arranged at one or more corners of the at least one inner wall facing the front surface of the mobile device. The second UV light source may be arranged at one or more of the corners of the inner wall facing the rear surface of the mobile device.

In some implementations, the UV light source may include: a first UV light source arranged on one inner side wall facing one side surface of the mobile device, among the inner side walls of the slot; and a second UV light source arranged on the other inner side wall facing the other side surface of the mobile device, among the inner side walls of the slot. In this case, the charging apparatus may further include: a first reflecting plate arranged on an inner wall of the slot, facing the rear surface of the mobile device, and configured to reflect UV light to the rear surface of the mobile device; and a second reflecting plate arranged on an inner wall of the slot, facing the front surface of the mobile device, and configured to reflect UV light to the front surface of the mobile device.

In some implementations, the UV light source may include: a first UV light source arranged at a first corner of an inner wall of the slot such that UV light has a path parallel to the rear surface of the mobile device; and a second UV light source arranged at a second corner of an inner wall of the slot such that UV light has a path parallel to the front surface of the mobile device. In this case, the charging apparatus may further include: a first light guide plate arranged on an inner wall of the slot, facing the rear surface of the mobile device, and configured to guide UV light emitted from the first UV light source such that the UV light is surface-emitted onto the rear surface of the mobile device; and a second light guide plate arranged on an inner wall of the slot, facing the front surface of the mobile device, and configured to guide UV light emitted from the second UV light source such that the UV light is surfaced-emitted onto the front surface of the mobile device.

In some implementations, the UV light source may be installed on an inner side surface of the slot so as to face a side surface of an object, and installed close to any one of the front and rear surfaces of the object.

In some implementations, the charging apparatus may include a power supply trigger device configured to control power to be automatically supplied to the UV light source when the mobile device is mounted in the slot. The charging apparatus may further include an openable and closable door to expose or cover the slot, and power may be supplied to the UV light source arranged in the slot in a state where the power supply trigger device is operated and the door is closed.

In some implementations, the charging apparatus may further include a support for supporting the mobile device such that the mobile device is mounted upright in the slot.

In another aspect, a multi-station charging apparatus for a mobile device based on the disclosed technology can include: a charging apparatus case including a slot into which a mobile device is inserted and mounted, wherein the front and rear surfaces of the mobile device are exposed in the slot; a multi-station device arranged at both side surfaces of the slot; and a UV light source configured to irradiate UV light onto the front and rear surfaces of the mobile device, which are exposed in the slot.

In some implementations, the multi-station charging apparatus may further include a charging port arranged at the bottom of the charging apparatus case. The charging port may include any one of a wired charging port and a wireless charging port.

In some implementations, the UV light source may include a UV LED. More specifically, in some implementations, such a UV light source may emit UV light at a wavelength of 100 nm to 400 nm.

In some implementations, the UV light source may include: a first UV light source arranged on an inner wall facing the front surface of the mobile device, and configured to irradiate UV light onto the front surface of the mobile device; and a second UV light source arranged on an inner wall facing the rear surface of the mobile device, and configured to irradiate UV light onto the rear surface of the mobile device. The first UV light source may be arranged at one or more of the corners of the inner wall facing the front surface of the mobile device. The second UV light source may be arranged at one or more of the corners of the inner wall facing the rear surface of the mobile device.

In some implementations, the one UV light source may include: a first UV light source arranged on one inner side wall facing one side surface of the mobile device; and a second UV light source arranged on the other inner side wall facing the other side surface of the mobile device. In this case, the multi-station charging apparatus may further include: a first reflecting plate arranged on an inner wall of the slot, facing the rear surface of the mobile device, and configured to reflect UV light to the rear surface of the mobile device; and a second reflecting plate arranged on the inner wall of the slot, facing the front surface of the mobile device, and configured to reflect UV light to the front surface of the mobile device.

In some implementations, the UV light source may include: a first UV light source arranged at a first corner of an inner wall of the slot such that UV light has a path parallel to the rear surface of the mobile device; and a second UV light source arranged at a second corner of an inner wall of the slot such that UV light has a path parallel to the front surface of the mobile device. In this case, the multi-station charging apparatus may further include: a first light guide plate arranged on an inner wall of the slot, facing the rear surface of the mobile device, and configured to guide UV light emitted from the first UV light source such that the UV light is surface-emitted onto the rear surface of the mobile device; and a second light guide plate arranged on an inner wall of the slot, facing the front surface of the mobile device, and configured to guide UV light emitted from the second UV light source such that the UV light is surface-emitted onto the front surface of the mobile device.

In some implementations, the multi-station charging apparatus may further include a power supply trigger device configured to control power to be automatically supplied to the UV light source, when the mobile device is mounted in the slot.

In some implementations, the multi-station charging apparatus may further include a support for supporting the mobile device such that the mobile device is upright mounted in the slot.

In some implementations, the multi-station device may include a speaker.

DETAILED DESCRIPTION

Figure 1:
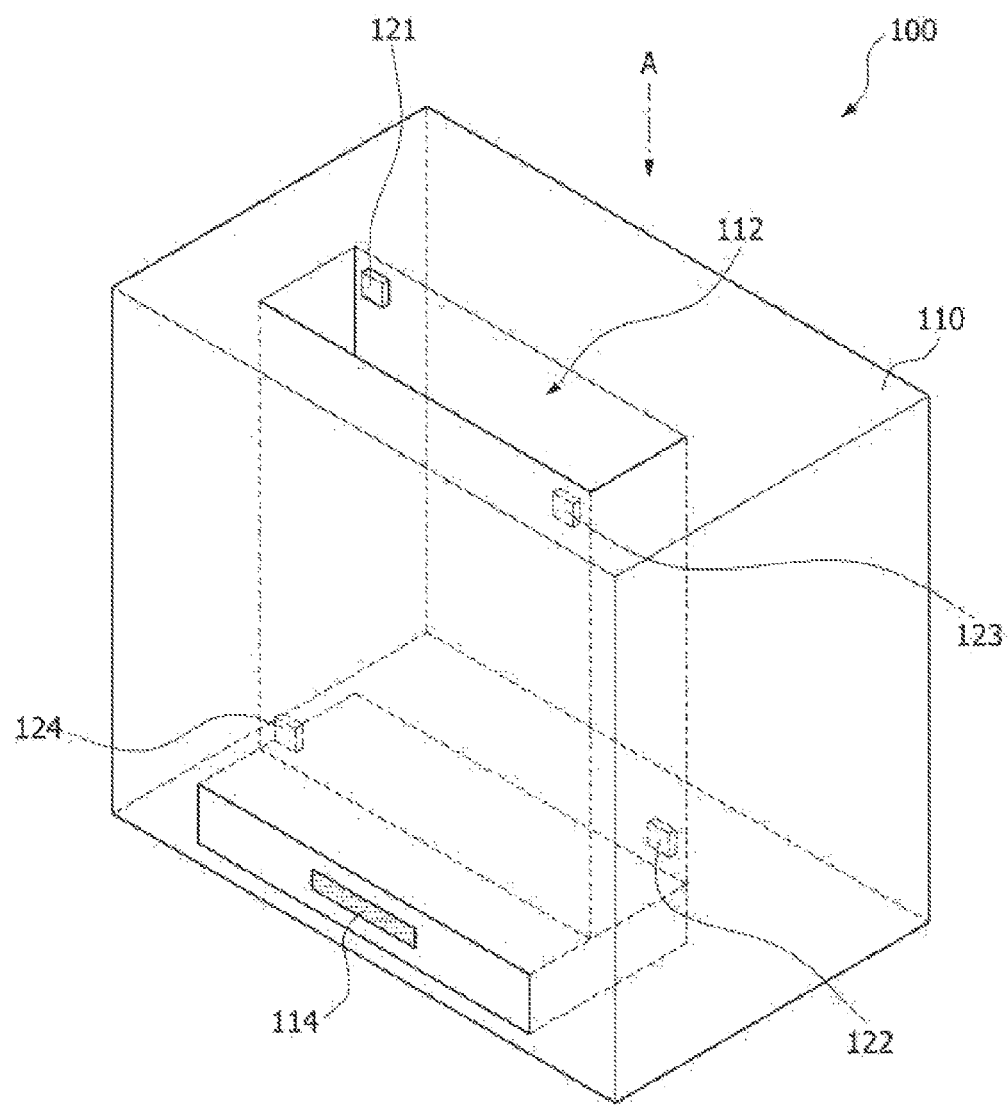
FIG. 1 is a diagram illustrating an exemplary charging apparatus for a mobile device in accordance with an embodiment of the disclosed technology.

Mobile devices are carried around and used by user everywhere and thus are prone to being infected with harmful germs such as bacteria and viruses. It is desirable, therefore, to disinfect the mobile devices to reduce or eliminate germs. The disclosed technology provides charging apparatuses for mobile devices that include one or more UV light sources to provide a sterilization function, thus allowing sterilizing a mobile device that is being charged via UV illumination.

Various charging apparatuses for a mobile device have a structure in which a wired port or a wireless port is arranged adjacent to the lower end of the charging apparatuses and a support structure for supporting a mobile device is arranged to be inclined by a predetermined angle. In such charging apparatuses for a mobile device, the mobile device is charged through the wired port or wireless port in a state where the mobile device is mounted or docked such that the rear surface of the mobile device is brought into contact with the surface of the support structure. The mobile device mounted or docked on a charging apparatus in this way is exposed only on the front surface of the mobile device. Therefore, even when sterilization treatment via UV illumination could be performed for the mobile device while the mobile device is mounted on the charging apparatus, sterilization process tend to be carried out in a restricted manner that sterilizes only the front surface of the mobile device. The disclosed technology can used to provide improve sterilization of mobile devices via UV illumination.

Exemplary embodiments of the disclosed technology are described below in more detail with reference to the accompanying drawings. The disclosed technology may, however, be embodied in different forms and should not be constructed as limited to the specific embodiments set forth in this patent document. Throughout the disclosure, like reference numerals refer to like parts throughout the various figures and embodiments of the disclosure.

First Embodiment

Figure 2:
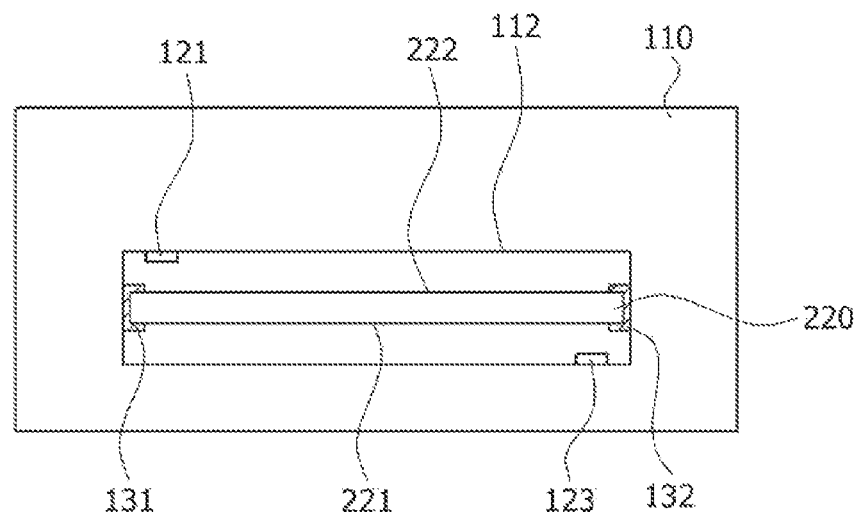
FIG. 2 is a diagram illustrating an exemplary shape of the charging apparatus for a mobile device, when seen from a top-down direction A of FIG. 1.

FIG. 1 is a diagram illustrating an exemplary charging apparatus for charging and sterilizing a mobile device in accordance with an embodiment of the described technology. FIG. 2 is a diagram illustrating an exemplary shape of the charging apparatus for charging and sterilizing a mobile device, when seen from a top-down direction A of FIG. 1.

Referring to FIGS. 1 and 2, the charging apparatus 100 for charging and sterilizing a mobile device in accordance with the first embodiment of the described technology may include a charging apparatus case 110 including a slot 112 structured to have an opening through the top surface of the charging apparatus case 110 to receive a mobile device 220 inserted through the opening of the slot 112 and mounted or docked inside the slot 112. In the present embodiment, the mobile device 220 is inserted and mounted or docked in the slot 112, but this is only an example. The described technology may be applied to incorporate a front door through which a mobile device can be mounted or docked, for example. Furthermore, FIG. 1 illustrates that the opening of the slot 112 through the top surface can be left open at all times. However, an openable and closable door may be further provided at the top surface opening of the slot 112 to selectively open and close the opening of the slot 112. Furthermore, the charge apparatus case 110 is shown to have a rectangular box shape, but may be formed in another shape conducive to receiving a mobile device for charging and sterilizing. In the present embodiment, the mobile device 220 inserted and mounted or docked in the slot 112 may be placed upright as illustrated in FIG. 1, and both of the front and rear surfaces 221 and 222 of the mobile device 220 may be exposed as illustrated in FIG. 2. That is, the front surface 221 of the mobile device 220 may be separated at a predetermined interval from the inner wall of the slot 112, and the rear surface 222 of the mobile device 220 may also be separated at a predetermined interval from the inner wall of the slot 112.

The mobile device 220 may be supported by support structures 131 and 132. The support structures 131 and 132 may physically support both side surfaces of the mobile device 220 such that the mobile device 220 is mounted or docked upright. The support structures 131 and 132 may be formed of a material transmitting UV light, for example, PMMA having a high monomer ratio. The mobile device 220 may be physically supported using other methods or structures. For example, the bottom of the mobile device 220 may be detachably supported. Regardless of the support structures or methods used, as the mobile device 220 is inserted into the slot 112, the mobile device 220 may be fixed or stabilized and physically supported. In the mounted or docked state, when the mobile device 220 is pressed down, the mobile device 220 may be released from the mounted or docked state to protrude from the slot 112. As the mobile device 220 is inserted and mounted or docked in the slot 112, a charging port of the mobile device 220 may be electrically connected to a charging system of the charging apparatus to allow the charging apparatus to charge the mobile device 220.

The slot 112 may have multiple UV light sources such as UV light sources 121, 122, 123, and 124 arranged on the inner walls of the slot 112. The UV light sources 121, 122, 123, and 124 may be arranged to include first UV light sources 121 and 122 disposed on one inner wall and second UV light sources 123 and 124 disposed on another inner wall. The first UV light sources 121 and 122 may be arranged on an inner wall facing the rear surface of the mobile device 220, among the inner walls of the slot 112, and irradiate UV light onto the rear surface of the mobile device 220. The second UV light sources 123 and 124 may be arranged on an inner wall facing the front surface of the mobile device 220, among the inner walls of the slot 112, and irradiate UV light onto the front surface of the mobile device 220. The first UV light sources 121 and 122 may be arranged at two corners in a diagonal direction among the corners of the inner wall facing the rear surface of the mobile device 220. Similarly, the second UV light sources 123 and 124 may also be arranged at two corners in a diagonal direction among the corners of the inner wall facing the front surface of the mobile device 220. However, the number and positions of the UV light sources may be changed in various manners. For example, on each inner wall, four UV light sources can be disposed with one at each of the four corners. Also, UV light sources can be disposed on the two side inner walls facing the respective side surfaces of the mobile device to irradiate the respective sides surfaces of the mobile device.

The UV light sources 121, 122, 123, and 124 may include a UV light emitting diode (LED). In this case, the UV LED may be provided as a module. The UV light sources 121, 122, 123, and 124 may emit UV light at a wavelength of 100 nm to 400 nm. The UV light emitted at a wavelength of 100 nm to 400 nm from the UV light sources 121, 122, 123, and 124 may sterilize at least the front and rear surfaces 221 and 222 of the mobile device 220 at substantially the same time. Although not illustrated, a UV light reflecting plate may be additionally arranged in the slot 112 to substantially uniformly form irradiation paths of the UV light emitted from the UV light sources 121, 122, 123, and 124 on the front surface 221 and the rear surface 222 of the mobile device 220. When UV light sterilization is performed within a predetermined space inside the slot 112, for example, the rate of sterilization when the UV light reflecting plate is installed on the inner wall surfaces defining the space is higher by 2 log than when the UV light reflecting plate is not installed. Furthermore, a protective layer formed of a UV light-transmitting material may be further arranged inside the slot 112 to protect the UV light sources 121, 122, 123, and 124 from external pollutants. The protective layer may include a PMMA layer having a high monomer ratio. Power for the UV light sources 121, 122, 123, and 124 may be manually supplied by a user, or automatically supplied according to whether the mobile device 220 is inserted and mounted or docked. When the power is automatically supplied, a power supply trigger device may be arranged in the charging apparatus case 110. For example, when the mobile device 220 is mounted or docked in the slot 112, power may be automatically supplied to the UV light sources 121, 122, 123, and 124 by the power supply trigger device.

Furthermore, when a door is provided in order to prevent UV light from being exposed to the outside and to prevent dust from being introduced into the slot 112, the power supply trigger device may be operated as the mobile device 200 is inserted. Furthermore, only when the door is closed, power may be supplied to the UV light sources to irradiate UV light.

The charging apparatus case 110 may have a charging port 114 arranged at the bottom. In the present embodiment, the charging port 114 may be arranged at the bottom of the front surface of the charging apparatus case 110. However, this is only an example, and the charging port 114 may be arranged at another position, for example, a side surface of the charging apparatus case 110. Regardless of the position or location of the charging port 114, the charging port 114 may be electrically connected to the charging system in the charging apparatus case 110. Thus, the charging port 114 may be electrically connected to the charging apparatus for the mobile device 220, for example, a battery through the charging system. The charging port 114 may include a wired charging port or wireless charging port. The charging port 114 may include both a wired charging port and a wireless charging port. Furthermore, although not illustrated, a charging terminal may be provided at a position corresponding to the position at which a charging connection terminal of the mobile device is inserted when the mobile device 220 is inserted into the slot 112, for when the charging port is a wired charging terminal. In this example, the charging terminal and the connection terminal of the mobile device may be conveniently coupled to each other only by inserting the mobile device 200 along the supports 131 and 132.

Second Embodiment

Figure 3:
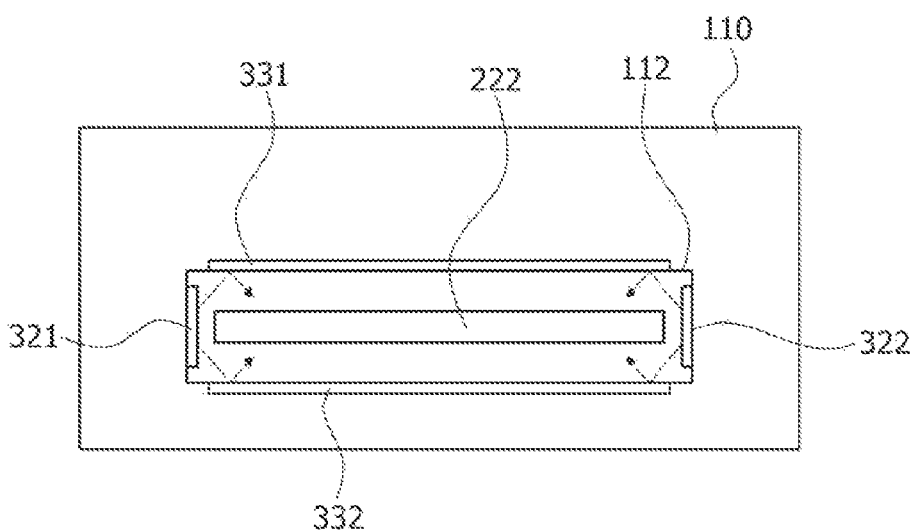
FIG. 3 is a diagram illustrating an exemplary shape of a charging apparatus for a mobile device in accordance with another embodiment of the described technology, when seen from the top-down.

FIG. 3 is a diagram illustrating an exemplary shape of a charging apparatus for a mobile device in accordance with another embodiment of the described technology, when seen from the top-down. In FIG. 3, the same reference numerals as those of FIGS. 1 and 2 represent like elements. Thus, the duplicated descriptions are omitted.

Referring to FIG. 3, the slot 112 may have UV light sources 321 and 322 arranged on the inner walls of the slot 112. The UV light sources 321 and 322 may be arranged to include a first UV light source 321 and a second UV light source 322. The first UV light source 321 may be arranged on a first inner wall facing one side surface of the mobile device 220, among the inner walls of the slot 112. The second UV light source 322 may be arranged on a second inner wall facing the other side surface of the mobile device 220, among the inner walls of the slot 112. Although not illustrated, multiple first UV light sources 321 may be vertically arranged on the first inner wall of the slot 112 so as to be separated from each other. Similarly, multiple second UV light sources 322 may also be vertically arranged on the second inner wall of the slot 112 so as to be separated from each other.

In the present embodiment, the slot 112 may include first and second reflecting plates 331 and 332 arranged on the inner wall facing the rear surface of the mobile device 220 and the inner wall facing the front surface of the mobile device 200, respectively. As indicated by dotted lines in the FIG. 3, the first and second reflecting plates 331 and 332 may control UV light paths to reflect UV light emitted from the first and second UV light sources 321 and 322 onto the rear and front surfaces of the mobile device 220.

The first and second UV light sources 321 and 322 may include a UV LED. In this example, the UV LED may be provided as a module. The first and second UV light sources 321 and 322 may emit UV light at a wavelength of 100 nm to 400 nm. The UV light emitted at a wavelength of 100 nm to 400 nm from the first and second UV light sources 321 and 322 may sterilize the front and rear surfaces 221 and 222 of the mobile device 220 at substantially the same time. Although not illustrated, a protective layer formed of a UV light-transmitting material may be further arranged inside the slot 112 to protect the first and second UV light sources 321 and 322 from external pollutants. Power for the first and second UV light sources 321 and 322 may be manually supplied by a user, or automatically supplied according to whether the mobile device 220 is inserted and mounted or docked. When power is automatically supplied, a power supply trigger device may be arranged in the charging apparatus case 110. In this example, when the mobile device 220 is mounted or docked in the slot 112, power may be automatically supplied to the first and second UV light sources 321 and 322 by the power supply trigger device.

Third Embodiment

Figure 4:
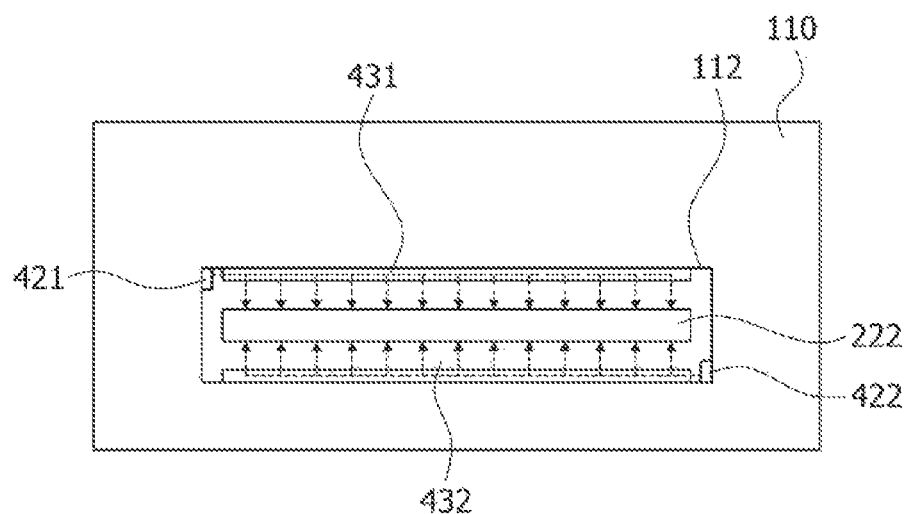
FIG. 4 is a diagram illustrating an exemplary shape of an apparatus for charging a mobile device in accordance with another embodiment of the described technology, when seen from the top-down.

FIG. 4 is a diagram illustrating an exemplary shape of an apparatus for charging a mobile device in accordance with another embodiment of the described technology, when seen from the top-down. In FIG. 4, the same reference numerals as those of FIGS. 1 and 2 represent like elements. Thus, the duplicated descriptions are omitted.

Referring to FIG. 4, the slot 112 may have UV light sources 421 and 422 arranged at corners facing each other on the inner walls of the slot 112. FIG. 4 shows an example where the UV light sources 421 and 422 are arranged at opposite corners diagonally facing each other. The UV light sources 421 and 422 may be arranged to include a first UV light source 421 disposed on one inner wall surface and a second UV light source 422 disposed on another inner wall surface. The first UV light source 421 may be arranged at a first corner of one of the inner walls of the slot 112. The first UV light source 421 may be arranged in such a manner that UV light emitted from the first UV light source 421 has a path substantially parallel to the rear surface of the mobile device 222. The second UV light source 422 may be arranged at a second corner of another one of the inner walls of the slot 112. The second UV light source 422 may be arranged in such a manner that UV light emitted from the second UV light source 422 has a path substantially parallel to the front surface of the mobile device 222. Although not illustrated, multiple first UV light sources 421 may be vertically arranged at the first corner of one of the inner walls of the slot 112 so as to be separated from each other. Similarly, multiple second UV light sources 422 may also be vertically arranged at the second corner of one of the inner walls of the slot 112 so as to be separated from each other.

On a first inner wall facing the rear surface of the mobile device 220 and a second inner wall facing the front surface of the mobile device 200, first and second light guide plates 431 and 432 may be provided. As indicated by dotted lines in FIG. 4, the first and second light guide plates 431 and 432 may guide UV light emitted from the first and second UV light sources 421 and 422 such that the UV light is substantially uniformly surface-emitted onto the rear and front surfaces of the mobile device 220.

The first and second UV light sources 421 and 422 may include a UV LED. In this example, the UV LED may be provided as a module. The first and second UV light sources 421 and 422 may emit UV light at a wavelength of 100 nm to 400 nm. The UV light emitted at a wavelength of 100 nm to 400 nm from the first and second UV light sources 421 and 422 may sterilize the front and rear surfaces 221 and 222 of the mobile device 220 at substantially the same time. Although not illustrated, a protective layer formed of a UV light-transmitting material may be further arranged inside the slot 112 to protect the first and second UV light sources 421 and 422 from external pollutants. Power for the first and second UV light sources 421 and 422 may be manually supplied by a user, or automatically supplied according to whether the mobile device 220 is inserted and mounted or docked. When power is automatically supplied, a power supply trigger device may be arranged in the charging apparatus case 110. In this example, when the mobile device 220 is mounted in the slot 112, power may be automatically supplied to the first and second UV light sources 421 and 422 by the power supply trigger device.

Fourth Embodiment

Figure 5:
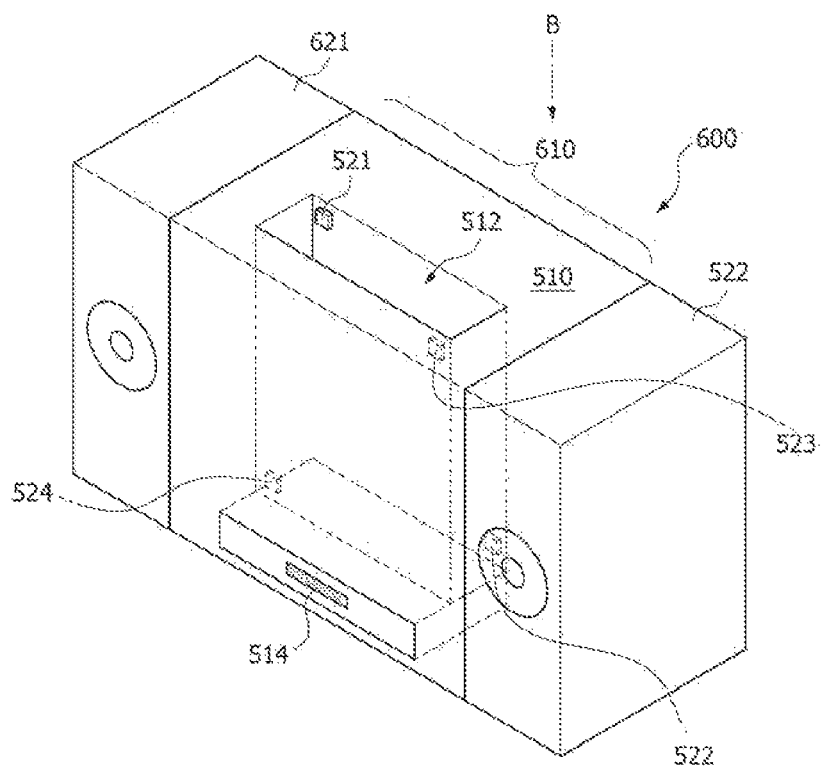
FIG. 5 is a diagram illustrating an exemplary multi-station charging apparatus for a mobile device in accordance with another embodiment of the described technology.
Figure 6:
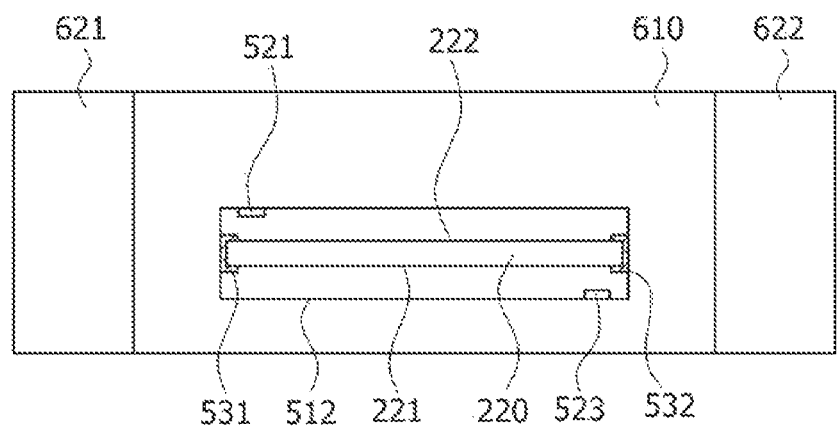
FIG. 6 is a diagram illustrating an exemplary shape of the multi-station charging apparatus for a mobile device, when seen from a top-down direction B of FIG. 5.

FIG. 5 is a diagram illustrating an exemplary multi-station charging apparatus for a mobile device in accordance with another embodiment of the described technology. FIG. 6 is a diagram illustrating an exemplary shape of the multi-station charging apparatus for a mobile device, when seen from a top-down direction B of FIG. 5.

Referring to FIGS. 5 and 6, the multi-station charging apparatus 600 for a mobile device in accordance with the embodiment of the described technology may include a charging apparatus case 510 and a multi-station device. The charging apparatus case 510 may include a slot 512 structured to receive the mobile device 220 inserted and mounted or docked into the slot 512. The multi-station device may be arranged at any position(s) surrounding, near or in contact with the charging apparatus case 510 to provide multiple functionalities to the mobile device 220 in addition to charging and sterilizing the mobile device 220. For example, the multi-station device can be arranged to be at both sides of the slot 512 as shown in FIGS. 5 and 6. The multi-station device may include speakers 621 and 622. However, this is only an example, and the multi-station device may include other devices in addition to the speakers 621 and 622 that can provide multiple functionalities to the mobile device 220. In the present embodiment, the mobile device 220 is inserted and mounted or docked in the slot 512, but this is only an example. The described technology may be used in an application in which a mobile device is mounted or docked through a front door, for example. Furthermore, the charge apparatus case 510 is shown in FIGS. 5 and 6 as having a rectangular box shape, but may be formed in any other shape conducive to receiving a mobile device. The front and rear surfaces 221 and 222 of the mobile device 220 inserted and mounted or docked in the slot 512 may be exposed to the outside. That is, the front surface 221 of the mobile device 220 may be separated at a predetermined interval from the inner wall of the slot 512, and the rear surface 222 of the mobile device 220 may also be separated at a predetermined interval from the inner wall of the slot 512.

The mobile device 220 may be supported by support structures 531 and 532. The support structures 531 and 532 may physically support both side surfaces of the mobile device 220 such that the mobile device 220 is mounted or docked upright. However, the mobile device 220 may be physically supported using different structures or methods. For example, the bottom of the mobile device 220 may be detachably supported. Regardless of the support structure or mechanism used, as the mobile device 220 is inserted into the slot 512, the mobile device 220 may be stabilized or fixed and physically supported. In this docked or mounted state, when the mobile device 220 is pressed down, the mobile device 220 may be released to protrude from the slot 512. As the mobile device 220 is inserted and mounted or docked in the slot 512, a charging port of the mobile device 220 may be electrically connected to a charging system of the charging apparatus.

The slot 512 may have UV light sources 521, 522, 523, and 524 arranged on the inner wall of the slot 512. The UV light sources 521, 522, 523, and 524 may be arranged to include first UV light sources 521 and 522 and second UV light sources 523 and 524. The first UV light sources 521 and 522 may be arranged on an inner wall facing the rear surface of the mobile device 220, among the inner walls of the slot 512, and irradiate UV light onto the rear surface of the mobile device 220. The second UV light sources 523 and 524 may be arranged on an inner wall facing the front surface of the mobile device 220, among the inner walls of the slot 512, and irradiate UV light onto the front surface of the mobile device 220. The first UV light sources 521 and 522 may be arranged at two corners in a diagonal direction among the corners of the inner wall facing the rear surface of the mobile device 220. Similarly, the second UV light sources 523 and 524 may also be arranged at two corners in a diagonal direction among the corners of the inner wall facing the front surface of the mobile device 220. However, the number and positions of the UV light sources may be changed in various manners. For example, on each inner wall, four UV light sources can be disposed with one at each of the four corners. Also, UV light sources can be disposed on the two side inner walls facing the respective side surfaces of the mobile device to irradiate the respective sides surfaces of the mobile device. In the multi-station charging apparatus for a mobile device in accordance with the embodiment of the described technology, the UV light sources may be arranged according to the structure described with reference to FIGS. 3 and 4.

The UV light sources 521, 522, 523, and 524 may include a UV LED. In this case, the UV LED may be provided as a module. The UV light sources 521, 522, 523, and 524 may emit UV light at a wavelength of 100 nm to 400 nm. The UV light emitted at a wavelength of 100 nm to 400 nm from the UV light sources 521, 522, 523, and 524 may sterilize the front and rear surfaces 221 and 222 of the mobile device 220 at substantially the same time. Although not illustrated, a UV light reflecting plate may be additionally arranged inside the slot 512 to substantially uniformly form irradiation paths of the UV light emitted from the UV light sources 521, 522, 523, and 524 on the front surface 221 and the rear surface 222 of the mobile device 220. Furthermore, a protective layer formed of a UV light-transmitting material may be further arranged inside the slot 512 to protect the UV light sources 521, 522, 523, and 524 from external pollutants. Power for the UV light sources 521, 522, 523, and 524 may be manually supplied by a user, or automatically supplied according to whether the mobile device 220 is inserted and mounted or docked. When the power is automatically supplied, a power supply trigger device may be arranged in the charging apparatus case 510. In this example, when the mobile device 220 is mounted or docked in the slot 512, power may be automatically supplied to the UV light sources 521, 522, 523, and 524 by the power supply trigger device.

The charging apparatus case 510 may have a charging port 514 arranged at the bottom of the charging apparatus case 510. In the present embodiment, the charging port 514 may be arranged at the bottom of the front surface of the charging apparatus case 510. However, this is only an example, and the charging port 514 may be arranged at another position of the charging apparatus case 510. Regardless of the position of the charging port 514, the charging port 514 may be electrically connected to the charging system in the charging apparatus case 510. Thus, the charging port 514 may be electrically connected to the charging apparatus for the mobile device 220, for example, a battery through the charging system. The charging port 514 may include a wired charging port or wireless charging port. The charging port 514 may include both a wired charging port and a wireless charging port.

Fifth Embodiment

Figure 7:
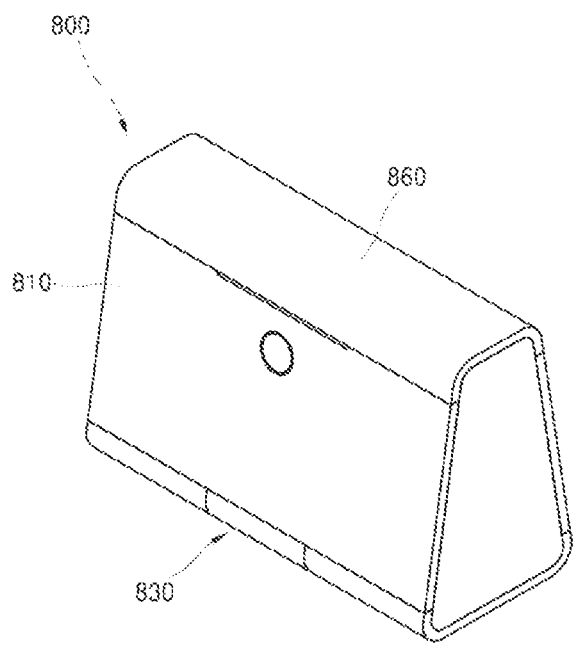
FIG. 7 is a perspective view of an exemplary charging apparatus for a mobile device in accordance with an embodiment of the described technology.
Figure 8:
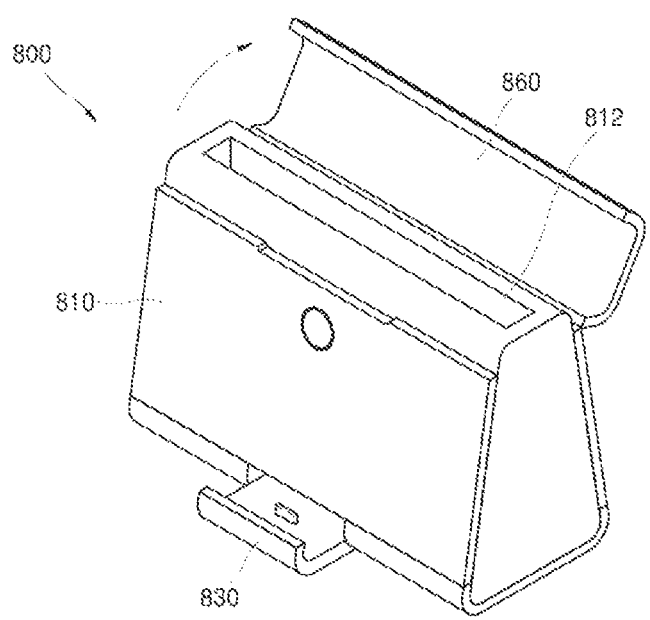
FIG. 8 is a perspective view illustrating an exemplary state in which a door of a charging apparatus for a mobile device is opened and a slide dock is drawn or moved forward.
Figure 9:
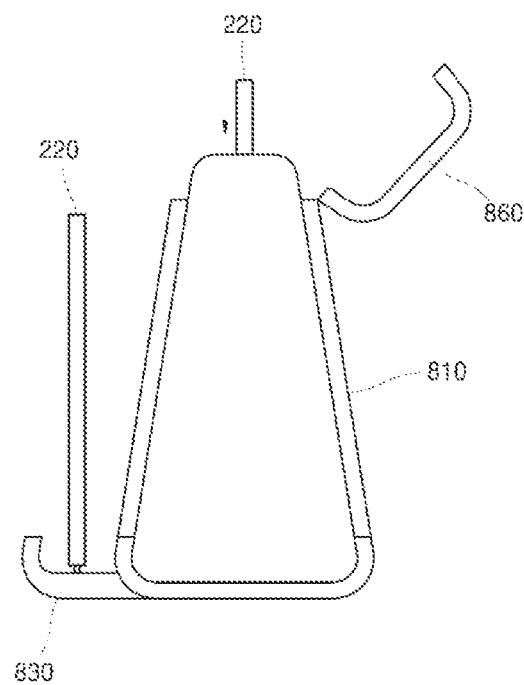
FIG. 9 is a side view illustrating a mobile device inserted into the charging apparatus of FIG. 8.
Figure 10:
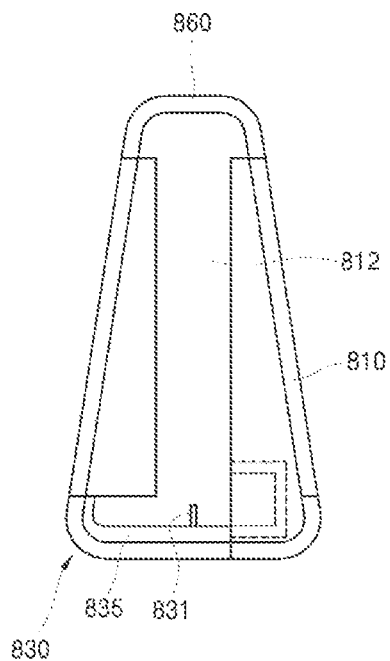
FIG. 10 is a side cross-sectional view of an intermediate part of the charging apparatus of FIG. 7.
Figure 11:
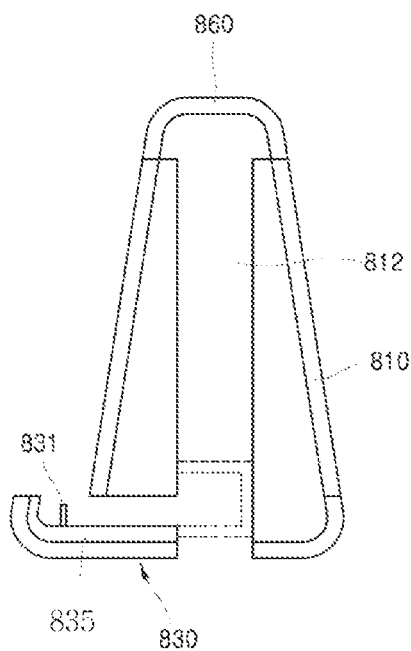
FIG. 11 is a side cross-sectional view illustrating an exemplary state in which the slide dock of the charging apparatus of FIG. 10 is drawn forward.
Figure 12:
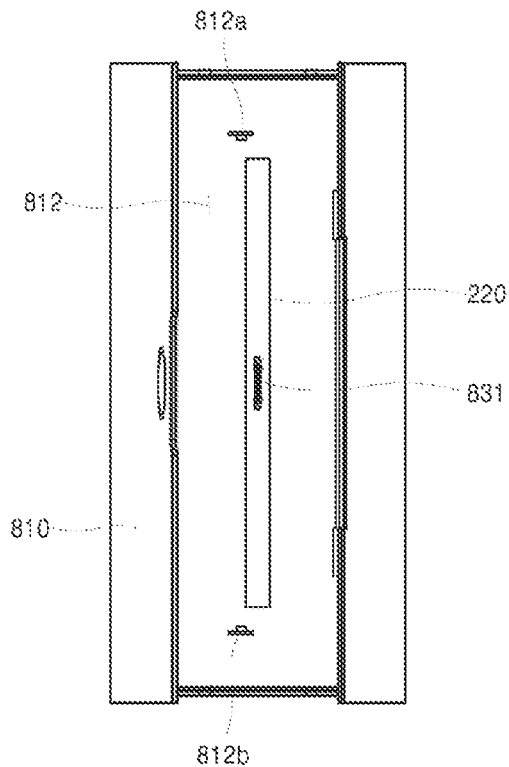
FIG. 12 is a plan view illustrating the inside of a slot in an exemplary state where the door of the charging apparatus of FIG. 7 is removed.

FIG. 7 is a perspective view of an exemplary charging apparatus for a mobile device in accordance with an embodiment of the present invention. FIG. 8 is a perspective view illustrating an exemplary state in which a door of the charging apparatus for a mobile device is opened and a slide dock is drawn or moved forward. FIG. 9 is a side view illustrating a mobile device inserted into the charging apparatus of FIG. 8. FIG. 10 is a side cross-sectional view of an intermediate part of the charging apparatus of FIG. 7. FIG. 11 is a side cross-sectional view illustrating an exemplary state in which the slide dock of the charging apparatus of FIG. 10 is drawn or moved forward. FIG. 12 is a plan view illustrating the inside of a slot in a state where the door of the charging apparatus of FIG. 7 is removed.

Referring to FIGS. 7 through 11, the charging apparatus 800 for a mobile device in accordance with the embodiment of the described technology may include a case 810, a door 860 movably covering the top of the case 810, and a charging unit 830 formed at the bottom of the case 810. The door 860 may be turned or hinged about one point of the rear top surface of the case 810 so as to be opened by rotating the door about the hinged point towards the back. The charging unit 830 may include a slide dock 835 which can be drawn or moved forward from the bottom of the case or pushed into the bottom of the case.

The top of the case may be opened using the door 860. When the door 860 is turned or rotated about the hinged point, the top of the case may be exposed. The slot 812 may be provided on the exposed top surface of the case. The slot 812 may include a UV light reflecting plate installed on an inner surface of the slot 812.

As illustrated in FIG. 9, the mobile device 220 may be placed in the slot 812 or on the slide dock 835 drawn or moved forward.

As illustrated in FIG. 10, the slot 812 may be housed in the case 810, and the top of the slot 812 may be opened by opening the door 860. The slot 812 may have a charging terminal 831 provided at the bottom of the slot 812, and the charging terminal 831 can be attached to and detached from a charging connection terminal of the mobile device 220 as the mobile device 220 is inserted into and removed from the slot 812 to mount and dismount the mobile device 220. Since the charging terminal is positioned at near the middle of the bottom of the slot in the front and rear direction of the slot, a predetermined interval or space may be formed between the inner wall of the slot and the front or rear surface of the mobile device in a state where the mobile device 220 is coupled to the charging terminal. Although not illustrated in FIGS. 10 and 11, a guide formed of a material capable of transmitting UV light may be provided in the slot 812 so as to guide the mobile device to connect with the charging terminal.

As illustrated in FIGS. 10 and 11, the charging terminal 831 may be installed on the slide dock 835. When the slide dock 835 is pushed into the case 810, the charging terminal 831 and the slot 812 may be aligned with each other to receive the mobile device 220 as illustrated in FIG. 10. Furthermore, when slide dock 835 is drawn or moved forward, the charging terminal 831 may be exposed to the front of the case 810 as illustrated in FIG. 11.

Regardless of whether the slide dock 835 is pushed into or drawn out of the case 810 or whether the door 860 is opened or closed, power may be supplied to the charging terminal 831 at all times when desired. Thus, when the slide dock 835 is pushed into the case 810 as illustrated in FIG. 10, the mobile device 220 may be charged in a state where the mobile device 220 is placed in the slot 812. Furthermore, when the slide dock 835 is drawn or moved out of the case 810 as illustrated in FIG. 11, the mobile device 220 may be charged in a state where the mobile device is placed on the charging terminal 831 exposed to the front of the case 810 and outside of the slot 812.

In order to prevent a mobile device from being inserted undesirably deep into the slot 812 and to intuitively inform a user that the slot 812 should be used, when the slide dock 835 is drawn forward, a stopper indicated by a dotted line in FIGS. 10 and 11 may be moved together with the slide dock 835 or operated in connection with the operation of the slide dock 835. When the stopper is positioned in the slot 812, the insertion of the mobile device 220 may be restricted. Thus, the user may intuitively recognize that the mobile device 220 cannot be charged through the slot.

Although not illustrated, another charging terminal may be further provided at the rear side of the charging terminal 831, that is, at the position indicated by the dotted lines in FIGS. 10 and 11), instead of the stopper illustrated in FIGS. 10 and 11. In this example, when the slide dock 835 is drawn or moved forward, the charging terminal 831 may be exposed to the front of the case 810 and outside of the slot 812, and the other charging terminal may be aligned with the slot 812. In another embodiment, the charging terminal 831 may be fixed to be aligned with the slot 812, and another charging terminal to be drawn moved may be provided at the front of the charging terminal 831. In this example, when the slide dock is drawn or moved forward, only the charging terminal to be drawn or moved may be drawn or moved forward with the slide dock 835. Furthermore, as long as such an embodiment is proposed through the described technology, various embodiments may be provided based on such an embodiment. Furthermore, while components such a charging terminal is illustrated as a wired port in the drawings, the charging terminal may be implemented with a wireless port.

Referring to FIG. 12, multiple first and second UV light sources 812a and 812b may be vertically arranged on both inner surfaces of the slot 812 so as to irradiate UV light toward an object inserted in the slot 812. As illustrated in FIG. 12, the first and second UV light sources 812a and 812b may not be arranged at the center of the side surface of the mobile device 220, but arranged at a position slightly forward or towards the front surface. This structure considers that the front surface of a mobile device such as a tablet PC or smart phone, which is more frequently touched than the rear surface, has a larger number of germs or a higher pollution level than the rear surface.

Although not illustrated, a power supply trigger device, which is operated when a mobile device is placed in the slot, may be arranged in the slot 812. In this example, power may be supplied to the UV light sources only in a state where the mobile device is placed in the slot 812, or supplied to the UV light sources only in a state where the door 860 is closed while the mobile device 220 is placed in the slot 812.

Sixth Embodiment

Figure 13:
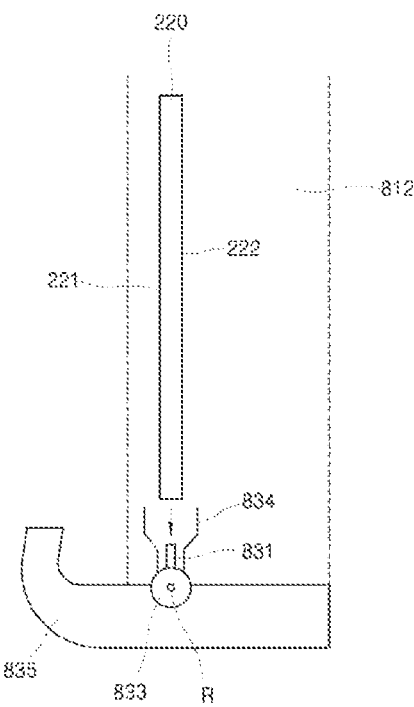
FIGS. 13 and 14 are side views illustrating an exemplary slide dock in accordance with another embodiment of the described technology.
Figure 14:
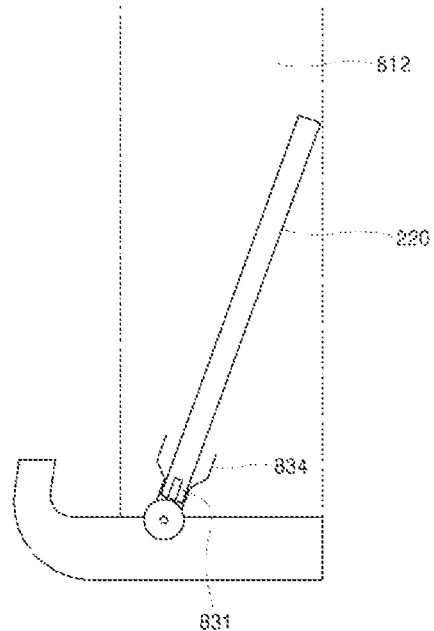
Figure 15:
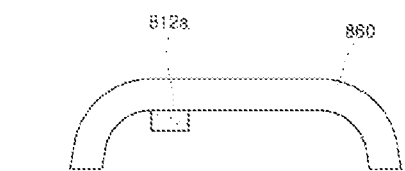
FIGS. 15 and 16 are side cross-sectional views illustrating exemplary arrangement positions of UV light sources in the charging apparatus of FIG. 7.
Figure 15:
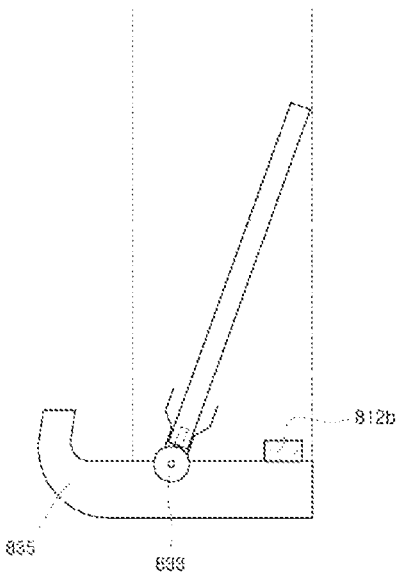
Figure 16:
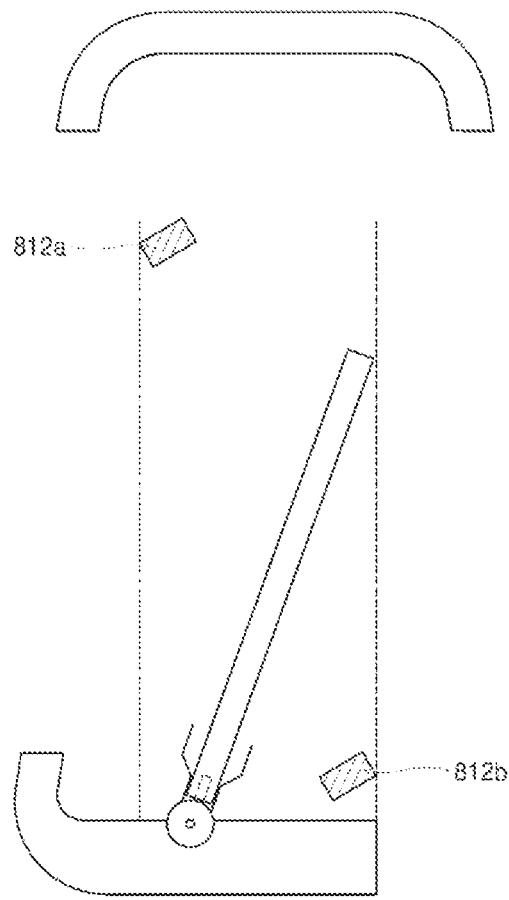
Figure 17:
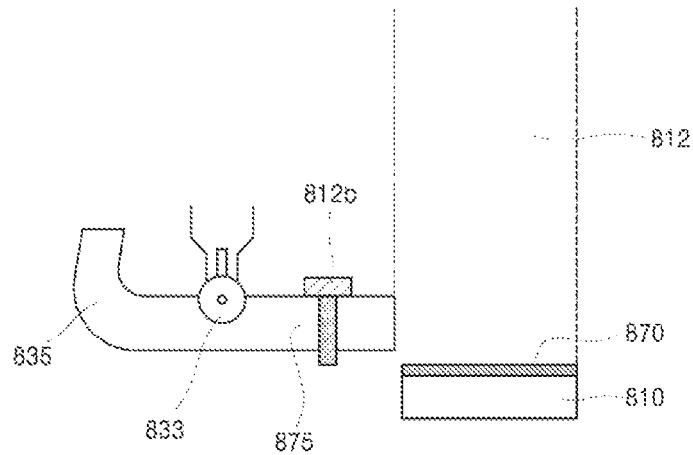
FIG. 17 is a diagram illustrating an exemplary power supply control structure in accordance with an embodiment of the described technology.

FIGS. 13 and 14 are side views illustrating an exemplary slide dock in accordance with another embodiment of the described technology. FIGS. 15 and 16 are side cross-sectional views illustrating exemplary arrangement positions of UV light sources in the charging apparatus of FIG. 7. FIG. 17 is a diagram illustrating an exemplary power supply control structure in accordance with an embodiment of the described technology.

The descriptions of the structure illustrated in FIGS. 13 to 16 will be focused on any differences from the descriptions of FIGS. 7 through 11.

FIGS. 13 and 14 illustrate an exemplary state in which the slide dock 835 is pushed into the case 812. Referring to FIGS. 13 and 14, the charging terminal 831 may be installed on a rotating drum 833 which rotates about an axis R with respect to the slide dock 835. Thus, when the rotating drum 833 is rotated, the charging terminal 831 may be rotated together as illustrated in FIG. 14. The rotating drum 833 may be rotated between the position at which the charging terminal 831 is placed upright and the position at which the charging terminal 831 is inclined towards the back of the case at a predetermined angle. The rotating drum 833 may be elastically supported by an elastic body (not illustrated) so as to be rotated toward a position at which the charging terminal 831 is placed upright. If necessary, a damper may be installed in addition to the elastic body. In this example, when the rotating drum 833 is rotated by the elastic force, the rotating drum 833 may be slowly rotated at a controlled speed. Furthermore, the rotating drum 833 may have a guide 834 installed so as to guide a mobile device to the charging terminal. The charging terminal may include a wired charging terminal and/or a wireless charging terminal.

Thus, when a user places the mobile device 220 at the regular position through the guide 834 while inserting the mobile device 200 into the slot 812 as illustrated in FIG. 13 and then slightly leans the mobile device 200, a moment may occur because the center of gravity of the mobile device is eccentrically positioned at the rear side of the rotation axis R. Then, such a moment may overcome the elastic force of the elastic body (not illustrated) so as to lean the mobile device 220 and the rotating drum 833 to the rear side, and the mobile device 220 may be obliquely placed to be slightly slanted as illustrated in FIG. 14. On the other hand, when the mobile device 220 is picked up, the mobile device 220 may be slightly lifted in a state shown in FIG. 14. Then, the rotating drum 833 may be returned to the original position of FIG. 13 by the elastic force of the elastic body (not illustrated). In such a structure, when the slide dock 835 is drawn or moved forward to mount an object on the charging terminal exposed to the front of the case, the object may be obliquely placed to lean against the front surface of the case.

In such a structure in which the mobile device 220 is obliquely placed to be slightly slanted, a first UV light source 812a may be installed on the door 860 or installed at the top of the front inner wall of the slot 812, and a second UV light source 812b may be installed on the slide dock 835 or installed at the bottom of the rear inner wall of the slot, as illustrated in FIG. 15 or 16. Then, an object may be obliquely placed to be slightly slanted, and the UV light sources may be positioned in the opposite diagonal direction of the oblique direction of the object inserted into the slot 812 so as to irradiate UV light onto both surfaces of the object inserted into the slot 812.

Such a structure, in which the mobile device is obliquely placed to be slightly slanted and the UV light sources are positioned in the opposite diagonal direction of the oblique direction of the mobile device in order to irradiate UV light on both surfaces of the mobile device, which may reduce the width of the slot and reliably sterilize both surfaces of the mobile device through UV light. A structure in which an object is placed upright may require a predetermined interval or space between either surface of the object and the inner wall of the slot 812. However, in the structure in which a mobile device is obliquely placed in accordance with the embodiment of the described technology, the slot 812 may be formed to be slimmer or smaller.

Furthermore, when UV LEDs are used as the UV light sources, a secondary optic (lens or light guide plate) may be provided at the front of the UV LEDs so as to properly control the diffusion angle and beam angle of UV light. Thus, UV light may be substantially uniformly and efficiently irradiated on the surface of the object.

Furthermore, a power supply trigger device (not illustrated) may be integrally installed on the rotating drum 833. In this case, when the rotating drum 833 is placed upright as illustrated in FIG. 13, the power supply trigger device may not be operated. When the rotating drum 833 is rotated backward at a predetermined angle as illustrated in FIG. 14, the power supply trigger device may be operated. Then, power may be supplied only to the slot 812 in which a mobile device is mounted on the rotating drum 833 and inclined backward, and UV light may be then irradiated onto the mobile device. Furthermore, only when the door is closed, power may be supplied to the UV light sources.

Although not illustrated, when the slide dock 835 is drawn or moved out of the case such that the charge terminal 831 is exposed to the front of the case 812, no power needs to be supplied to the UV light source 812b exposed to the outside of the case 812 in the structure in which the UV light sources are installed on the door 860 and the slide dock 835 as illustrated in FIG. 15. Thus, as illustrated in FIG. 17, a power supply rail 870 may be installed on the case 810, and a power connection unit 875 may be installed at each UV light source 821b. In this case, when the slide dock 835 is drawn or moved forward, the power connection unit 875 may be isolated from the power supply rail 870 so as to block the power supply to the UV light source 812b exposed to the outside. Besides, the position of the slide dock 835 may be detected for an electric circuit to control whether to turn on the UV light source.

In accordance with the embodiments of the described technology, a mobile device may be mounted or docked on the charging apparatus such that the front and rear surfaces are exposed in the charging apparatus, and the UV light sources may be arranged to irradiate UV light onto the exposed front and rear surfaces of the mobile device. Thus, both surfaces of the mobile device may be sterilized at substantially the same time, in a state where the mobile device is mounted or docked in the charging apparatus.

Only a few embodiments, implementations and examples are described and other embodiments and implementations, and various enhancements and variations can be made based on what is described and illustrated in this document.

What is claimed is:

1. A charging apparatus for charging a mobile device, the charging apparatus comprising:
    a charging apparatus case including a slot structured to receive a mobile device into the slot, wherein front and rear surfaces of the mobile device are exposed to inner walls of the slot;
    at least one UV light source disposed on at least one of the inner walls of the slot and configured to irradiate UV light onto the front and rear surfaces of the mobile device, which are exposed to the inner walls of the slot; and
    a slide dock moveable between:
        a first position in which a charging terminal on the slide dock is inside the charging apparatus case and accessible to the mobile device by insertion of the mobile device in the slot, and
        a second position in which the charging terminal on the slide dock is outside the charging apparatus case and not accessible to the mobile device by insertion of the mobile device in the slot.

2. The charging apparatus of claim 1, further comprising:
a charging port arranged at a bottom of the charging apparatus case.

3. The charging apparatus of claim 2,
    wherein the charging apparatus case includes a slide dock installed on the charging apparatus case, the slide dock is configured to move between an inner predetermined position of the charging apparatus case and a position outside the charging apparatus case,
    wherein the charging port is installed on the slide dock, and
    wherein a charging terminal installed on the slide dock is exposed to the outside in a state where the slide dock is drawn to the outside from the inside of the charging apparatus case.

4. The charging apparatus of claim 3, further comprising:
a stopper interworking with movement of the slide dock,
    wherein, when the slide dock is drawn to the outside from inside of the charging apparatus case, the stopper is positioned in a slot having no corresponding charging terminal.

5. The charging apparatus of claim 2,
    wherein a guide for guiding an object in the slot to a position of the charging port is installed in the slot, and
    wherein the guide is formed of a material that transmits UV light.

6. The charging apparatus of claim 2,
    wherein the charging port is installed on a rotating drum which rotates about an axis, and
    wherein, when the rotating drum is rotated, the mobile device connected to the charging port is rotated integrally with rotation of the rotating drum, and is obliquely placed in the slot.

7. The charging apparatus of claim 6,
wherein the rotating drum is rotated between at least first and second positions, and
wherein an elastic body is installed on the rotating drum, the elastic body elastically supporting the rotating drum in a direction where the rotating drum is rotated from the second position to the first position.

8. The charging apparatus of claim 6,
wherein the rotating drum is rotated between at least first and second positions, and
wherein the rotating drum includes a power supply trigger device which is triggered when the rotating drum is located at the second position, to supply power to the UV light source.

9. The charging apparatus of claim 3,
    wherein one of the charging apparatus case and the slide dock, which are movable relative to each other, includes a power supply rail installed, and the other one not including the power supply rail includes power connection units connected to the at least one UV light source arranged in the slot, and
    wherein, according to a relative position between the charging apparatus case and the slide dock, the power connection units are contacted with or isolated from the power supply rail.

10. The charging apparatus of claim 1, wherein the at least one UV light source includes a UV LED.

11. The charging apparatus of claim 1, wherein the UV light source includes:
    a first UV light source arranged on an inner wall facing the front surface of the mobile device and configured to irradiate UV light onto the front surface of the mobile device; and
    a second UV light source arranged on an inner wall facing the rear surface of the mobile device and configured to irradiate UV light onto the rear surface of the mobile device.

12. The charging apparatus of claim 11, wherein the at least one UV light source is arranged at one or more corners of the at least one inner wall.

13. The charging apparatus of claim 1, wherein the at least one UV light source comprises:
a first UV light source arranged on one inner side wall of the slot facing one side surface of the mobile device; and
a second UV light source arranged on the other inner side wall of the slot facing the other side surface of the mobile device.

14. The charging apparatus of claim 13, further comprising:
a first reflecting plate arranged on an inner wall of the slot, facing the rear surface of the mobile device, and configured to reflect UV light to the rear surface of the mobile device; and
a second reflecting plate arranged on an inner wall of the slot, facing the front surface of the mobile device, and configured to reflect UV light to the front surface of the mobile device.

15. The charging apparatus of claim 1, wherein the at least one UV light source comprises:
a first UV light source arranged at a first corner of an inner wall of the slot such that UV light has a path substantially parallel to the rear surface of the mobile device; and
a second UV light source arranged at a second corner of an inner wall of the slot such that UV light has a path substantially parallel to the front surface of the mobile device.

16. The charging apparatus of claim 15, further comprising:
a first light guide plate arranged on an inner wall of the slot, facing the rear surface of the mobile device, and configured to guide UV light emitted from the first UV light source such that the emitted UV light is surface-emitted onto the rear surface of the mobile device; and
a second light guide plate arranged on an inner wall of the slot, facing the front surface of the mobile device, and configured to guide UV light emitted from the second UV light source such that the emitted UV light is surfaced-emitted onto the front surface of the mobile device.

17. The charging apparatus of claim 1, wherein the UV light source is installed on an inner side surface of the slot so as to face a side surface of an object, and installed close to one of the front and rear surfaces of the mobile device.

18. The charging apparatus of claim 1, further comprising a power supply trigger device configured to control power to be automatically supplied to the at least one UV light source when the mobile device is received into the slot.

19. The charging apparatus of claim 18, further comprising:
an openable and closable door to expose or cover the slot, wherein power is supplied to the at least one UV light source arranged in the slot in a state where the power supply trigger device is operated and the door is closed.

20. A multi-station charging apparatus for charging a mobile device, comprising:
a charging apparatus case including a slot structured to receive a mobile device, wherein the front and rear surfaces of the mobile device are exposed to inner walls of the slot;
a multi-station device arranged at both side surfaces of the slot;
at least one UV light source disposed on at least one of the inner walls of the slot and configured to irradiate UV light onto the front and rear surfaces of the mobile device, which are exposed to the inner walls of the slot; and
a slide dock moveable between:
a first position in which a charging terminal on the slide dock is inside the charging apparatus case and accessible to the mobile device by insertion of the mobile device in the slot, and
a second position in which the charging terminal on the slide dock is outside the charging apparatus case and not accessible to the mobile device by insertion of the mobile device in the slot.

21. A charging apparatus for charging a mobile device, the charging apparatus comprising:
a charging apparatus case including a slot structured to receive a mobile device into the slot, wherein, upon receiving the mobile device, front and rear surfaces of the mobile device are exposed to inner walls of the slot;
at least one UV light source disposed on at least one of the inner walls of the slot and configured to radiate UV light onto the front and rear surfaces of the mobile device exposed to the inner walls of the slot; and
a charging port arranged at a bottom of the charging apparatus case, and
wherein the charging apparatus case includes a slide dock installed on the charging apparatus case, the slide dock is configured to move between an inner predetermined position of the charging apparatus case and a position outside the charging apparatus case,
wherein the charging port is installed on the slide dock, and
wherein a charging terminal installed on the slide dock is exposed to the outside in a state where the slide dock is drawn to the outside from the inside of the charging apparatus case,
wherein the charging apparatus further comprises a stopper interworking with movement of the slide dock, and
wherein, when the slide dock is drawn to the outside from inside of the charging apparatus case, the stopper is positioned in a slot having no corresponding charging terminal.

22. A charging apparatus for charging a mobile device, the charging apparatus comprising:
a case including an upper portion selectively exposed by a cover;
a slot provided in the case to receive a mobile device and having an inner wall with a UV light source; and
a slide dock installed in a lower portion of the case to be movable between a first position inside the case and a second position outside the case;
a first charging terminal provided on the slide dock to be electrically connectable to the mobile device in accordance with the move of the slide dock; and
a second charging terminal provided at a rear side of the first charging terminal on the slide dock to be electrically connectable to the mobile device in accordance with the move of the slide dock.

23. The charging apparatus of claim 22, wherein the slot includes a UV light reflecting inner wall to provide an irradiation path of a UV light to the mobile device.

24. The charging apparatus of claim 22, wherein power is supplied to at least one of the first charging terminal or the second charging terminal.

25. The charging apparatus of claim 22, wherein either the first charging terminal or the second charging terminal is aligned with the slot.

\* \* \* \* \*